United States Patent
Achhammer et al.

(10) Patent No.: US 8,653,838 B2
(45) Date of Patent: Feb. 18, 2014

(54) SOOT SENSOR

(75) Inventors: Roland Achhammer, Beratzhausen (DE); Johannes Ante, Regensburg (DE); Rudolf Bierl, Regensburg (DE); Stephan Heinrich, Pfeffenhausen (DE); Markus Herrmann, Regensburg (DE); Wolfgang Lauerer, Laaber (DE); Andreas Ott, Steinsberg (DE); Willibald Reitmeier, Hohenschambach (DE); Denny Schädlich, Neustadt (DE); Manfred Weigl, Viehhausen (DE); Andreas Wildgen, Nittendorf (DE)

(73) Assignee: Continental Automotive GmbH, Hannover (DE)

( * ) Notice: Subject to any disclaimer, the term of this patent is extended or adjusted under 35 U.S.C. 154(b) by 399 days.

(21) Appl. No.: 12/967,368

(22) Filed: Dec. 14, 2010

(65) Prior Publication Data

US 2011/0156727 A1 Jun. 30, 2011

(30) Foreign Application Priority Data

Dec. 14, 2009 (DE) .................. 10 2009 058 260

(51) Int. Cl.
*G01R 27/08* (2006.01)
(52) U.S. Cl.
USPC ............................................... 324/691
(58) Field of Classification Search
USPC ....................................................... 324/691
See application file for complete search history.

(56) References Cited

U.S. PATENT DOCUMENTS

| | | | |
|---|---|---|---|
| 7,543,477 B2 | 6/2009 | Berger et al. | |
| 2001/0051108 A1 | 12/2001 | Schoenauer | |
| 2003/0196499 A1* | 10/2003 | Bosch et al. | 73/865.5 |
| 2007/0220968 A1* | 9/2007 | Tokuyasu et al. | 73/204.26 |
| 2008/0264146 A1* | 10/2008 | Roesch et al. | 73/23.33 |
| 2008/0283398 A1* | 11/2008 | Nelson et al. | 204/406 |
| 2009/0051376 A1 | 2/2009 | Schnell et al. | |
| 2009/0056416 A1* | 3/2009 | Nair et al. | 73/28.01 |
| 2009/0126458 A1 | 5/2009 | Fleischer et al. | |
| 2010/0051458 A1* | 3/2010 | Teranishi et al. | 204/424 |

FOREIGN PATENT DOCUMENTS

| | | | |
|---|---|---|---|
| AT | 501 386 B1 | 10/2008 | |
| DE | 199 59 871 A1 | 6/2001 | |
| DE | 10133384 * | 1/2003 | ............. G01N 27/04 |
| DE | 103 19 664 A1 | 11/2004 | |
| DE | 102004028997 | 1/2006 | |
| DE | 10 2005 029 219 A1 | 12/2006 | |
| DE | 10 2005 030 134 A1 | 1/2007 | |
| DE | 10 2006 047 927 A1 | 4/2008 | |
| DE | 10 2008 004 210 A1 | 7/2009 | |
| WO | WO 03/006976 A2 | 1/2003 | |

* cited by examiner

*Primary Examiner* — Jeff Natalini
(74) *Attorney, Agent, or Firm* — Cozen O'Connor

(57) ABSTRACT

A soot sensor for the detection of soot particles in an exhaust gas flow, having interdigitally engaged measurement electrodes applied on a substrate. An electrical resistance between the measurement electrodes is a measure of soot load of the exhaust gas flow. The measurement electrodes are divided into two regions, a first region in which no soot particles can be deposited and a second region where soot particles are deposited from the exhaust gas flow. The first region and the second region are exposed simultaneously to the other conditions prevailing in the exhaust gas flow.

10 Claims, 5 Drawing Sheets

SOOT SENSOR

BACKGROUND OF THE INVENTION

1. Field of the Invention

The invention relates to a soot sensor configured to detect soot particles in an exhaust gas flow having a structure comprising measurement electrodes engaging interdigitally with one another, which are applied on a substrate, the electrical resistance between the measurement electrodes being measured as a measure of a soot load of the exhaust gas flow.

2. Description of the Related Art

The buildup of pollutants from exhaust gases in the atmosphere is a topic of great discussion at present. Associated with this is the fact that the availability of fossil energy sources is limited. In response to this combustion processes in internal combustion engines are being thermodynamically optimized to improve their efficiency. In the automotive sector, this is reflected in the increasing use of diesel engines. The disadvantage of this combustion technology in relation to optimized gasoline engines, however, is a significantly increased output of soot. Soot is particularly carcinogenic due to the accumulation of polycyclic aromatics, which has already been responded to in various regulations. For example, exhaust gas emission standards with maximum limits for soot emission have been established. There is therefore a need for economical sensors which reliably measure the soot content in the exhaust gas flow of motor vehicles.

Soot sensors are used to measure the amount of soot instantaneously being output, so that the engine management in an automobile can receive information for a current driving situation to reduce the emission values by control technology adaptations. Furthermore, with the aid of soot sensors, active exhaust gas cleaning by exhaust gas soot filters can be initiated or exhaust gas may be recycled to the internal combustion engine. In the case of soot filtering, regenerable filters are used that filter a substantial part of the soot content from the exhaust gas. Soot sensors are required for the detection of soot, to monitor the function of the soot filters or control their regeneration cycles.

To this end, a soot sensor may be connected before and/or after the soot filter, which is also referred to as a diesel particle filter.

The sensor connected before the diesel particle filter is used to increase the system reliability and ensure operation of the diesel particle filter under optimal conditions. Since this depends to a great extent on the mass of soot accumulated in the diesel particle filter, it is very important to have an accurate measurement of the particle concentration before the diesel particle filter system, particularly in order to determine a high particle concentration before the diesel particle filter.

A sensor connected after the diesel particle filter offers the opportunity to carry out an on-board diagnosis, and furthermore serves to ensure optimal operation of the exhaust gas after-treatment system.

There have been various approaches for the detection of soot in the prior art. One approach that has been followed extensively in the laboratory is the use of light scattering by the soot particles. This procedure is very suitable for elaborate measuring instruments. When attempting to use them as a mobile sensor system in the exhaust gas system as well, it should be mentioned that these approaches for producing an optical sensor in a motor vehicle entail very high costs. Furthermore, unresolved problems remain in relation to the required optical windows being polluted by combustion exhaust gases.

Laid-open German patent specification DE 199 59 871 A1 discloses a sensor and an operating method for the sensor, both of which being based on thermal observations. The sensor comprises of an open porous shaped body, for example a honeycomb ceramic, a heating element and a temperature sensor. When the sensor is brought in contact with a volume of gas to be measured, soot is deposited on it. For the measurement, the soot deposited in a period of time is ignited with the aid of the heating element and burnt. The temperature increase resulting from the combustion is measured.

Particle sensors for conductive particles are currently known, in which two or more metal electrodes are provided which comprise measurement electrodes engaging in one another in a comb-like fashion, or interdigitally. Soot particles, which are deposited on these sensor structures, short circuit the measurement electrodes and therefore change the impedance of the electrode structure. With an increasing particle concentration on the sensor surface, a decreasing resistance, or an increasing current with a constant voltage applied between the measurement electrodes, can thereby be measured. Such a soot sensor is disclosed, for example, in DE 10 2004 028 997 A1.

The comb-like (interdigital) measurement electrode structure of these soot sensors is generally formed by thin conductor tracks lying next to one another. The conductor tracks have, for example, a spacing of 10 μm from one another. Besides the desired resistance change of the soot sensor due to soot loading of the comb-like structure consisting of measurement electrodes, the resistance of the soot sensor may also change owing to undesired short circuits. These undesired short circuits may be caused by a scratched or partially detached measurement electrode. The measured resistance value of the soot sensor would be vitiated by these undesired short circuits, which must then be established by regular function diagnosis of the soot sensor in order to comply with legal requirements in force for the reliability of exhaust gas after-treatment systems. Furthermore, the resistance values may be influenced by the substrate itself, on which the measurement electrodes are arranged. Above all, when the substrate is heated, currents can flow through the hot substrate from one measurement electrode to another. Undesired deposits, for example ash, may also allow currents that vitiate the measurement of the soot load to flow between the measurement electrodes.

SUMMARY OF THE INVENTION

It is therefore an object of one embodiment of the invention to provide a soot sensor, with which a faulty measurement can be identified in an economical fashion.

The structure comprising measurement electrodes engaging interdigitally in one another is divided into two regions, a first region in which no soot particles can be deposited and a second region where soot particles are deposited from the exhaust gas flow, the first region and the second region being exposed simultaneously to the other conditions prevailing in the exhaust gas flow, there is always a comparison region which cannot have its electrical properties modified by ash, short circuits due to mechanical damage, or metal particles from the combustion engine. All other changes to the properties of the soot sensor, however, are experienced simultaneously by both regions. First, the change in the temperature of the soot sensor both due to the hot exhaust gases and during the heating to regenerate the structure of the measurement electrodes, entails a change in the electrical resistance of the substrate. This resistance change takes place simultaneously both in the first region and in the second region, since the two regions are exposed simultaneously to the other conditions prevailing in the exhaust gas flow. The temperature-dependent resistance change of the substrate can therefore be determined and compensated for. Other conditions which change in the exhaust gas flow may be the moisture which acts on the sensor or the ageing of the substrate of the soot sensor in the course of its use. These changes can also lead to modified resistance values of the substrate, and can be detected owing to the inventive division of the soot sensor into a first region and a second region.

In one refinement of the invention, the substrate is ceramic. For example, it is possible to use aluminum oxide ($Al_2O_3$), zirconium oxide, silicon dioxide ($SiO_2$), LTCC (low temperature co-fired ceramics) or HTCC (high temperature co-fired ceramics). These materials have a high electrical resistance and withstand the high temperatures in the exhaust gas system.

In one embodiment of the invention, the structure comprising measurement electrodes engaging interdigitally in one another is constructed from thick-film electrodes. Robust electrode structures can be produced very economically by thick-film methods.

In another configuration, the structure of measurement electrodes engaging interdigitally in one another is constructed from thin-film electrodes. Very fine structures can be produced with high precision by thin-film methods, which makes it possible to produce a soot sensor with a high measurement sensitivity.

In one refinement of the invention, the first region is provided with a high-impedance cover layer. This cover layer may be silicon nitride, silicon dioxide ($SiO_2$), aluminum oxide ($Al_2O_3$), zirconium oxide, LTCC (low temperature co-fired ceramics) or HTCC (high temperature co-fired ceramics). Such a cover layer ensures that no soot particles can be deposited on the measurement electrodes of the first region. When freeing the measurement electrodes by heating, ash particles furthermore cannot remain behind in the first region on the structure of the measurement electrodes.

In this case, it may be advantageous for the first region to be provided with a cover layer having an accurately defined electrical resistance. If this accurately defined electrical resistance is known, it may be included in the comparative observations between the resistance values of the first region and those of the second region. It is then particularly advantageous for the temperature dependency of the resistance change of the cover layer to be known, and for it to be included in the comparative observations between the resistance values of the first region and those of the second region.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The present invention will be explained below with reference to the appended drawings with the aid of a preferred embodiment. This embodiment comprises a soot sensor for use in a motor vehicle.

DETAILED DESCRIPTION OF THE PRESENTLY PREFERRED EMBODIMENTS

Figure 1:
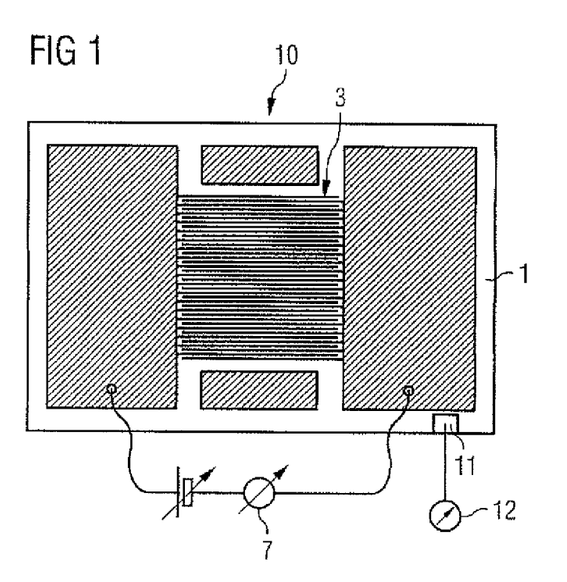
FIG. 1 is a soot sensor.

FIG. 1 shows a soot sensor 10 which is constructed from a substrate 1, a heating element 2 (FIG. 2) and a structure of measurement electrodes 3. The substrate 1 may be made of a ceramic material, or of another material which has electrically insulating properties and readily withstands the burn-off temperature of soot. In order to free the soot sensor 10 of soot by burning, the soot sensor 10 is typically heated with the aid of an electrical heating resistor to temperatures of between 500 and 800° C. The electrically insulating substrate 1 must tolerate these temperatures without damage. The structure of the measurement electrodes 3 is formed as a comb-like (interdigital) structure, an electrically insulating region of the substrate 1 always being visible between two measurement electrodes. The flow of current between the electrode structures is measured with the aid of a current measuring element 7. So long as the soot sensor 10 is entirely free of soot particles 4, only a very small direct current can be measured by the current measuring element 7, since between the measurement electrodes 3 there is always a region of the substrate 1 which has an electrically insulating effect and is not bridged by soot particles 4. FIG. 1 furthermore shows a temperature sensor 11 as a component of the soot sensor 10 with temperature evaluation electronics 12, that monitor the temperature prevailing in the soot sensor 10 particularly when burning the soot load off from the soot sensor 10. When burning off the soot using the electrical heating resistor, the substrate 1 is also heated to temperatures of between 500 and 800° C., with the resistance values of the substrate changing significantly toward high temperatures.

Figure 2:
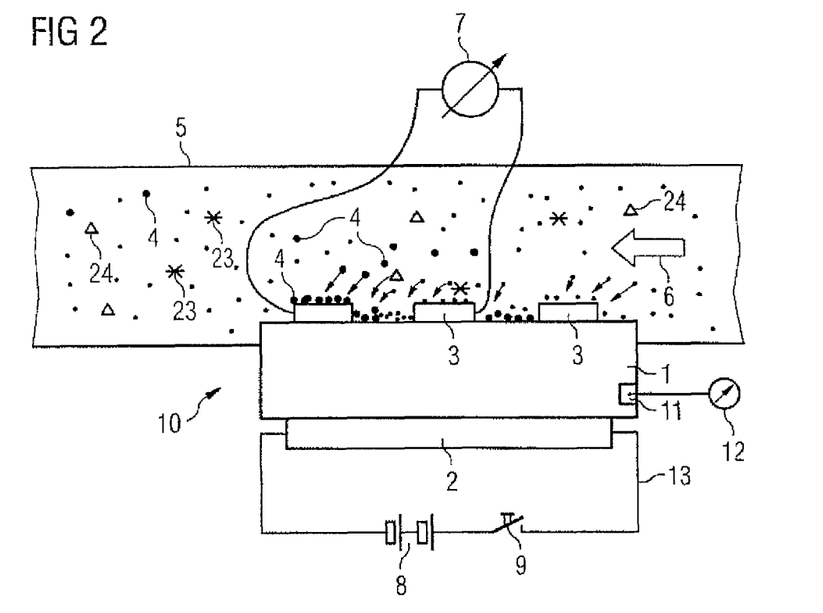
FIG. 2 depicts a mode of action of the soot sensor.

FIG. 2 now shows the mode of action of the soot sensor 10. Here, the soot sensor 10 is arranged in a tailpipe 5, through which an exhaust gas flow 6 laden with soot particles 4 flows. Besides the soot particles 4, the exhaust gas flow 6 may also contain other constituents, for example water 23, hydrocarbons 24, motor oil, metal particles from mechanical wear and/or ash components from burnt additives. The flow direction of the exhaust gas flow 6 is indicated by the arrow. The purpose of the soot sensor 10 is to measure the concentration of the soot particles 4 in the exhaust gas flow 6. To this end, the soot sensor 10 is arranged in the tailpipe 5 so that the structure of measurement electrodes 3 faces toward the exhaust gas flow 6 and therefore the soot particles 4. From the exhaust gas flow 6, soot particles 4 are deposited both on the measurement electrodes 3 and on the insulating regions of the substrate 1 in the gaps between the measurement electrodes 3. When enough soot particles 4 have been deposited on the insulating regions between the measurement electrodes 3, an increased direct current will flow between the measurement electrodes 3 owing to the conductivity of the soot particles 4, and this will be detected by the current measuring element 7. The soot particles 4 bridge the electrically insulating gaps between the measurement electrodes 3. In this way, the loading of the exhaust gas flow 6 with soot particles 4 can be measured by the soot sensor 10.

The soot sensor 10 in FIG. 2 also shows the heating element 2, which can be supplied with electric current from the heating current supply 8 by the heating current circuit 13. In order to heat the soot sensor 10 to the burn-off temperature of the soot particles 4, the heating current switch 9 is closed so that the heating element 2 heats up and the entire soot sensor 10 is therefore heated. Integrated in the soot sensor 10, there is a temperature sensor 11 which, with the aid of the temperature evaluation electronics 12, monitors the process of heating the soot sensor 10 and therefore the burn-off process of the soot particles 4. The electrical heating element 2 may be formed so that it can simultaneously be used as a temperature sensor 11.

The current measuring element 7, the temperature evaluation electronics 12 and the heating current switch 9 are represented here by way of example as discrete components, although these components may of course be part of a microelectronic circuit which, for example, is integrated in a controller for the soot sensor 10.

Figure 3:
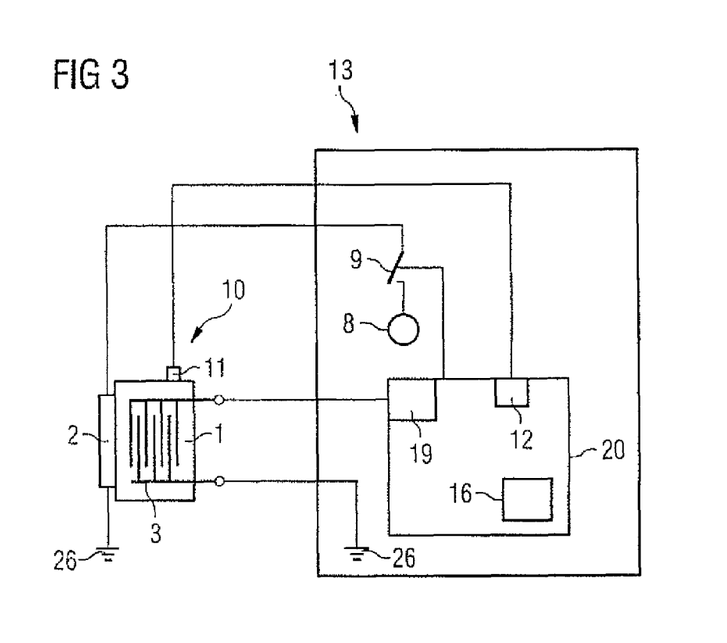
FIG. 3 is a schematic block diagram of an evaluation circuit permanently installed in a motor vehicle for on-board function diagnosis of the soot sensor.

FIG. 3 shows the evaluation circuit 13 permanently installed in a motor vehicle 15 for on-board function diagnosis of the soot sensor 10 and/or for the detection of further constituents in the soot. The soot sensor 10 comprises a measurement electrode structure inter-engaging in a finger-like fashion, which, in the case of an intact soot sensor 10, has no metallic short circuits. On and between the measurement electrodes 3, soot particles 4 are deposited during measurement operation of the sensor and lead to a flow of current between the measurement electrodes 3, which serves as a measure of the soot load of the exhaust gas flow. Beyond a certain amount of soot particles 4 deposited on the measurement electrodes 3, however, a maximum conductivity through the soot layer is achieved which cannot be increased further even with more deposition of soot. Beyond a certain amount of deposited soot particles, the soot sensor 10 is therefore "blind" to further measurement of the soot concentration in the exhaust gas. It is then necessary to regenerate the soot sensor 10 by burning the soot layer off from the measurement electrodes 3. To this end, a heating current is delivered from the heating current supply 8 to the heating element 2 by turning on the heating current switch 9. The soot sensor 10 is heated in a monitored fashion. The heating of the soot sensor 10 is monitored by the temperature sensor 11 formed on or in the soot sensor 10. The dependency of the soot sensor resistance or its conductivity (conductivity corresponds to the inverse of resistance) on the temperature on the soot sensor 10 may be recorded by the evaluation circuit 13. This forms the function of the resistance of the real soot sensor 10 with respect to its temperature. The function of the resistance of a fully intact soot sensor 10 with respect to its temperature may be recorded in the electronic memory 16. Besides the resistance change over the measurement electrode structure due to the deposition of soot particles, parasitic resistance changes also occur, owing for example to ash, metal particles or the significant conductivity increase of the substrate 1 when reaching high temperatures (beyond about 600° C.).

These functions describe the temperature coefficients of the real fully intact soot sensor 10. The significantly different temperature coefficients of intact and defective soot sensors result from the facts that carbon and therefore soot is a typical NTC conductor and metallic conductors are typical PTC conductors. The function of the resistance of the soot sensor 10 with respect to its temperature, and therefore its temperature coefficient, will depend on whether a metallic conduction process or the carbon/soot conduction dominates. It is then possible to compare the temperature coefficient measured on the second region of the soot sensor 10 with that of the first region, as with that of the intact soot sensor 10, and with the aid of this comparison to identify a defective soot sensor 10 and/or electronically compensate for the defects.

The temperature coefficient describes the relative change of a physical quantity as a function of the change in temperature relative to a reference temperature. The temperature coefficient of a resistor indicates the change in the resistance value of the resistor as a function of the temperature, and has the unit $K^{-1}$. The temperature coefficient is also referred to as the temperature factor of a resistor. For many, metallic resistor materials, the temperature coefficient is positive so that larger resistance values result from an increase of the applied temperature. In the case of the intact soot sensor 10, however, the temperature coefficient is negative because the resistance value of the intact sensor 10 is derived predominantly from the high electrical conductivity of the heated soot between the measurement electrodes 3. Here, it should be pointed out clearly that identification of the fault-free nature of the soot sensor 10 with the aid of the two-part structure of the measurement electrodes, which will be described in more detail below, can make a substantial contribution to monitoring and compliance with the exhaust gas regulations in force.

In the evaluation circuit 13 on the microcontroller 20, there is an electronic memory 16. The measured temperature coefficient of the soot sensor 10 may then be stored in the electronic memory 16. If the temperature coefficient of the soot sensor 10 in the second region, as measured by the evaluation circuit 13, is substantially greater than that of a fault-free soot sensor 10 (first region), the evaluation circuit 13 identifies the faulty nature of the soot sensor 10. A corresponding error signal may then be sent to a motor management system in the motor vehicle, the driver of the motor vehicle being prompted to replace the soot sensor 10 and the error being stored in the on-board diagnosis unit 22 (FIG. 4) of the motor vehicle.

Figure 4:
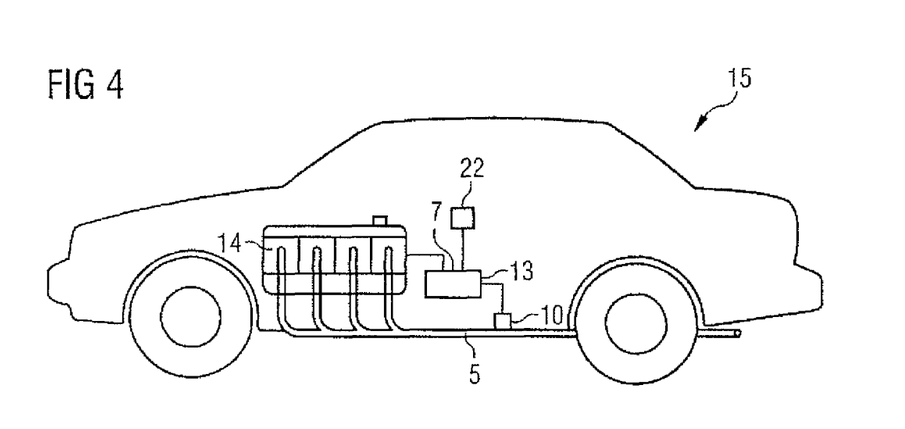
FIG. 4 is a motor vehicle having an internal combustion engine.

For general illustration of the overall system, FIG. 4 represents a motor vehicle 15 having an internal combustion engine 14. The internal combustion engine 14 discharges the exhaust gas flow 6 generated by it through a tailpipe 5. A soot sensor 10 is arranged in the tailpipe 5, and is connected to an evaluation circuit 13, which may also contain the current measuring element 7. The evaluation circuit 13 described in detail in FIG. 3 forwards the signals relating to faultiness of the soot sensor 10 and/or the findings concerning further constituents in the soot to the on-board diagnosis unit 22. Both the current measuring element 7 for measuring the soot load of the exhaust gas flow 6 and the evaluation circuit 13 for the on-board function diagnosis of a soot sensor 10 in a motor vehicle 15 may be formed on the same integrated electronic circuit.

Figure 5:
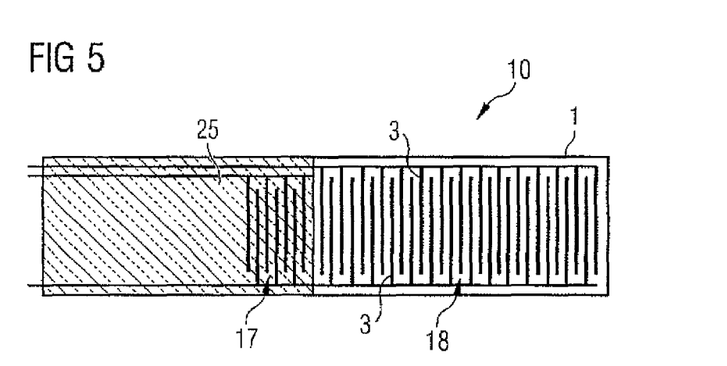
FIG. 5 is a view of a soot sensor in accordance with an embodiment of the present invention.

FIG. 5 shows the soot sensor 10 according to one embodiment of the invention, having a substrate 1 and the structure of measurement electrodes 3 engaging interdigitally in one another. The structure consisting of measurement electrodes 3 engaging interdigitally in one another is divided into a first region 17 and a second region 18. No soot particles can be deposited on the first region 17. The deposition of soot particles 4 takes place exclusively on the second region 18. For protection against the soot particles 4, the first region 17 is provided with a cover layer 25. This cover layer may consist for example of silicon nitride, silicon dioxide, aluminum oxide, zirconium oxide, LTCC or HTCC. The entire soot sensor 10 shown here is exposed to the exhaust gas flow 6 in the tailpipe 5. On the first region 17, neither soot particles 4 nor contaminants from the exhaust gas flow 6 can be deposited. On the second region 18, soot particles, ash particles and contaminants from the exhaust gas flow 6 can be deposited. In the phase of burning free, the structure consisting of measurement electrodes 3 engaging interdigitally in one another on the second region 18 is cleaned. Since, owing to the cover layer 25, no particles can be deposited on the measurement electrodes 3 on the first region 17, the measurement electrodes 3 in the first region 17 cannot be burnt free. The entire soot sensor 10, however, is exposed with its first region 17 and its second region 18 to the other conditions prevailing in the exhaust gas flow. One essential condition prevailing in the exhaust gas flow is the temperature, which also acts on the soot sensor 10. Particularly in the phase of burning free, the conductivity of the substrate 1 changes substantially. By comparing the resistance measurement values of the first region 17 with those of the second region 18, a conclusion can be drawn regarding the parasitic contamination of the second region 18.

Figure 6:
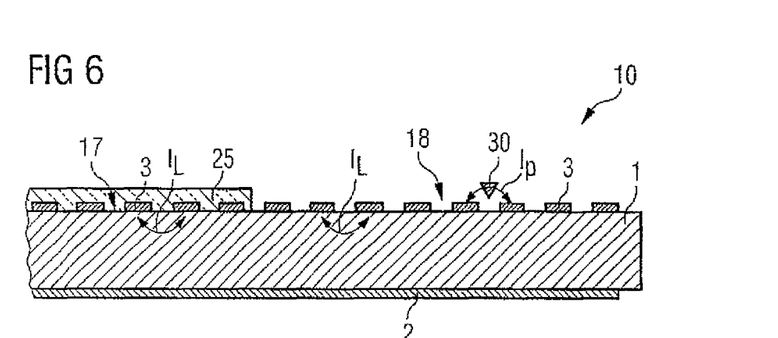
FIG. 6 is a side view of the soot sensor of FIG. 5.

FIG. 6 a side view of the soot sensor 10 of FIG. 5. The substrate 1 can be seen, on which the measurement electrodes 3 are arranged. The structure of measurement electrodes 3 engaging interdigitally in one another is again divided into first region 17 and second region 18. The first region 17 is covered with a cover layer 25. Here, $I_L$ denotes the leakage currents which can flow through the substrate 1 between the measurement electrodes 3. These leakage currents $I_L$ are particularly large when the substrate 1 is heated by the heating element 2 to the burn-off temperature of the soot. Yet since both the first region 17 and the second region 18 are heated simultaneously to the burn-off temperature of the soot, by comparing the resistance values over the structure consisting of measurement electrodes 3 in the first region 17 and over the structure consisting of measurement electrodes 3 in the second region 18, it is possible to identify whether parasitic currents $I_P$ have been formed. In FIG. 6, by way of example, a metal particle 30 is represented between two measurement electrodes 3 in the second region 18. The metal particle 30 enables a parasitic current $I_P$ to flow, which vitiates the measurement values of the soot sensor 10 since the additional parasitic current $I_P$ reduces the resistance value of the structure consisting of measurement electrodes 3 in the second region. By comparing the resistance values of the first region 17 with those of the second region 18, it is therefore possible to unequivocally identify a malfunction of the second region 18.

Figure 7:
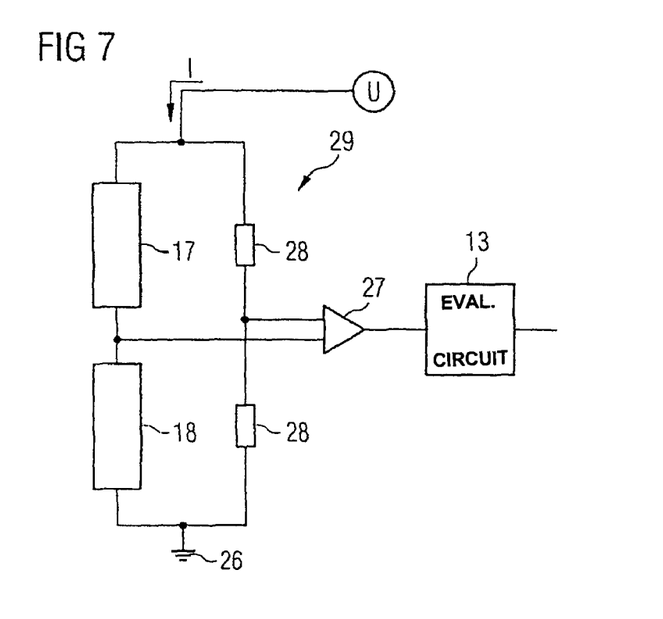
FIG. 7 is a schematic block diagram of an electronic circuit for evaluation of a soot sensor.

An electronic circuit 29 for the evaluation of a soot sensor 10 is represented in FIG. 7. Here, the schematically represented first region 17 and the schematically represented second region 18 are connected to two further electrical resistors 28 to form a Wheatstone bridge. The changes in the resistance values of the first region 17, and in particular of the second region 18, lead to detuning of the Wheatstone bridge, which can be identified with the aid of the operational amplifier 27. The signals delivered by the operational amplifier 27 are sent to the electronic evaluation circuit 13. As is usual in the case of Wheatstone bridges, a current I flows from a voltage source U, which is formed as a constant voltage source, through the resistors 17, 18 and 28 in the two branches of the Wheatstone bridge to a lower electrical potential, which is represented here as ground 26.

Figure 8:
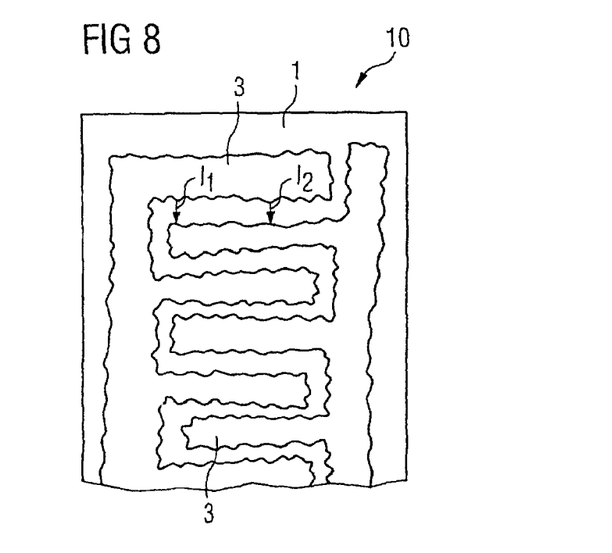
FIG. 8 is an enlarged representation of a part of the soot sensor.

FIG. 8 is an enlarged representation of a part of the soot sensor 10. The substrate 1 can be seen, on which the interdigitally inter-engaging measurement electrodes 3 are arranged. The measurement electrodes 3 may be configured in thin-film technology or thick-film technology. Specifically when configuring the measurement electrodes 3 in thick-film technology, it is very difficult to make the contours of the measurement electrodes 3 precise. The edge lines of the measurement electrodes 3 are represented in FIG. 8 as wavy lines, which is a relatively good approximation of the real edge profile of thick-film electrodes. It can be seen clearly that different current paths are formed between the measurement electrodes 3. In the first current path $I_1$ the effective distance between the measurement electrodes 3 is relatively large, so that relatively little current would flow here, and in the second current path $I_2$ the effective distance between the measurement electrodes 2 is very small, so that a high current would flow here. Particularly in the region of the second current path $I_2$, the occurrence of parasitic currents $I_P$ is very likely because even a small foreign particle can lead to strong short circuits in this region.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A soot sensor configured to detect soot particles in an exhaust gas flow, comprising:
    a substrate;
    a measurement electrode structure comprising interdigitally engaged electrodes applied to the substrate, wherein an electrical resistance between the interdigitally engaged electrodes is measured as a measure of the soot load of the exhaust gas flow, the measurement electrodes comprising:
        a first region where the soot particles cannot be deposited; and
        a second region where the soot particles are deposited from the exhaust gas flow; and
    a cover layer arranged on the interdigitally engaged electrodes in the first region, the cover layer:
        (i) being arranged with respect to the first region so that soot particles cannot be deposited between the part of the interdigitally engaged electrodes in the first region, and
        (ii) having a defined resistance so that a parasitic current of the interdigitally engaged electrodes in the second region is detected by a comparison between resistance values of the first region and resistance values of the second region,
        wherein the first region and the second region are simultaneously exposed to prevailing conditions in the exhaust gas flow.

2. The soot sensor as claimed in claim 1, wherein the substrate is ceramic.

3. The soot sensor as claimed claim 2, wherein the cover layer is a high-impedance cover layer.

4. The soot sensor as claimed in claim 2, wherein the ceramic comprises is at least one of aluminum oxide, zirconium oxide, silicon dioxide, low temperature co-fired ceramics, and high temperature co-fired ceramics.

5. The soot sensor as claimed in claim 4, wherein the measurement electrode structure is constructed from at least one of thick-film electrodes and thin-film electrodes.

6. The soot sensor as claimed claim 5, wherein the cover layer is a high-impedance cover layer.

7. The soot sensor as claimed in claim 6, wherein the cover layer comprises is at least one of silicon nitride, silicon dioxide, aluminum oxide, zirconium oxide, low temperature co-fired ceramics, and high temperature co-fired ceramics.

8. The soot sensor as claimed in claim 1, wherein the measurement electrode structure is constructed from thick-film electrodes.

9. The soot sensor as claimed in claim 1, wherein the measurement electrode structure is constructed from thin-film electrodes.

10. An electrical circuit for the evaluation of a soot sensor comprising:
   a soot sensor comprising:
      a substrate;
      a measurement electrode structure comprising interdigitally engaged electrodes applied to the substrate, wherein an electrical resistance between the interdigitally engaged electrodes is measured as a measure of a soot load of the exhaust gas flow, the measurement electrodes comprising:
         a first region where soot particles cannot be deposited; and
         a second region where the soot particles are deposited from the exhaust gas flow; and
      a cover layer arranged on the interdigitally engaged electrodes in the first region, the cover layer:
         (i) being arranged with respect to the first region so that soot particles cannot be deposited between the part of the interdigitally engaged electrodes in the first region, and
         (ii) having a defined resistance so that a parasitic current of the interdigitally engaged electrodes in the second region is detected by a comparison between resistance values of the first region and resistance values of the second region,
            wherein the first region and the second region are simultaneously exposed to prevailing conditions in the exhaust gas flow; and
         two further electrical resistances,
            wherein the first region, the second region, and the two further electrical resistances are connected to form a Wheatstone bridge.

* * * * *